United States Patent [19]

Michaelson et al.

[11] 4,390,739

[45] Jun. 28, 1983

[54] HYDROXYLATION OF OLEFINS

[75] Inventors: Robert C. Michaelson, Waldwick; Richard G. Austin, Ridgewood, both of N.J.

[73] Assignee: Exxon Research & Engineering Co., Florham Park, N.J.

[21] Appl. No.: 310,097

[22] Filed: Oct. 9, 1981

[51] Int. Cl.$^3$ .................... C07C 31/20; C07C 31/22; C07C 33/20; C07C 31/42
[52] U.S. Cl. ............................ 568/860; 260/397.2; 549/243; 560/186; 562/587; 568/458; 568/811; 568/821; 568/833; 568/838; 568/847
[58] Field of Search .............. 568/860, 458, 811, 821, 568/833, 838, 847; 562/587; 560/186; 549/243; 260/397.2

[56] References Cited

U.S. PATENT DOCUMENTS 3,232,957 2/1966 Sharp ............................ 568/860

FOREIGN PATENT DOCUMENTS 54-145604 11/1979 Japan .

Primary Examiner—Joseph E. Evans
Attorney, Agent, or Firm—Robert A. Maggio

[57] ABSTRACT

A process directed to the hydroxylation of olefins by reacting said olefins with an oxygen containing gas and water in the presence of a catalyst composition comprising (i) a catalytically active metal oxide such as $OsO_4$, (ii) as a co-catalyst I a transition metal salt such as $CuBr_2$, and (iii) optionally a co-catalyst II salt such as tetra ethyl ammonium bromide is disclosed.

9 Claims, No Drawings

HYDROXYLATION OF OLEFINS

BACKGROUND OF THE INVENTION

1. Field of the Invention

The present invention relates to a process for converting olefinically unsaturated compounds to their corresponding diols or polyols in the presence of a specifically defined oxidation catalyst composition, water, and an oxygen containing gas.

2. Description of the Prior Art

Processes for the production of glycols, such as ethylene glycol, from olefins are well known in the art. One class of these processes involves the conversion of an olefin, e.g., ethylene, to its corresponding oxide, e.g., ethylene oxide, as an intermediate. This intermediate is subsequently hydrolyzed to form the corresponding glycol. Prominent in this class of processes is a method wherein an olefinic compound is reacted with an organic hydroperoxide compound in the presence of a molybdenum catalyst to form the corresponding oxide. The organic hydroperoxide preferably is formed by reacting an aliphatic saturated compound with oxygen. The reaction scheme can be summarized as follows:

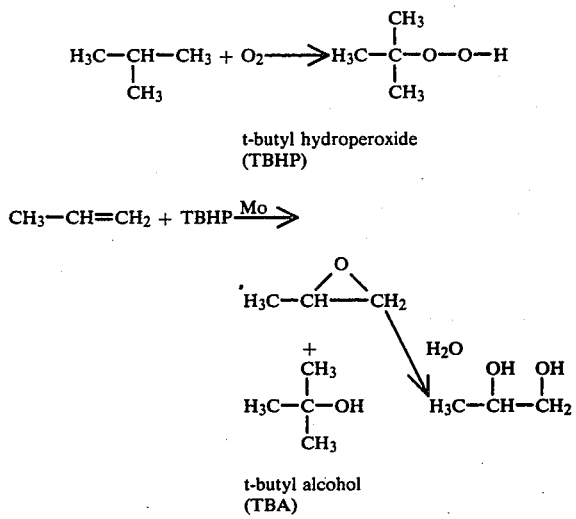

The commercial attractiveness of this process is dependent on the ability to use or sell the organic alcohol co-product. Given the fluctuation in economic conditions, however, it may be difficult to dispose of large quantities of these organic alcohol co-products in an economically attractive manner. In any event, it can be troublesome, when the quantity of one product, selected on the basis of marketing possibilities for a given period, necessarily determines the quantity of some other product which may be smaller or larger than desirable in view of changing marketing requirements within that same period. It can, therefore, under certain circumstances be considered as a disadvantage of the aforenoted process that such large quantities of organic alcohols are formed as co-products, even though under other circumstances the formation of two products may well be found acceptable.

An alternative multi-stage method for making ethylene glycol involves the oxidation of ethylene to ethylene oxide at elevated temperatures and pressure using oxygen and a silver containing catalyst. The ethylene oxide is then hydrated either catalytically using a diluted aqueous solution of a strong acid, or at high temperatures and pressures, with some diethylene and triethylene glycols being formed as by-products. Because, in the first reaction stage (i.e., ethylene to ethylene oxide) one molecule of oxygen theoretically forms one molecule of carbon dioxide from the ethylene, the maximum theoretical selectivity of this reaction is at best 85%. Moreover, the first stage of reaction requires very careful control of the operating conditions just to obtain selectivities in the range of 60 to 70%. Thus, rigid process control and by-product formation are disadvantages of this type of indirect glycol formation.

An alternative approach to glycol formation involves the catalytic oxidation of olefins directly to form the corresponding glycol without the formation of olefin oxide intermediates.

For example, it is well known from the technical literature and patents that olefins can be effectively directly oxidized with a strong oxidizing agent in the presence of catalytic amounts of osmium oxides, e.g., osmium tetroxide, e.g., to their corresponding glycols.

More specifically, Japanese Patent Application No. Sho 54-145604, published Nov. 14, 1979, is directed to a process for hydroxylating olefins in the presence of $OsO_4$, a quaternary ammonium salt such as tetra ethyl ammonium bromide, and a peroxide including organo peroxides and $H_2O_2$ as the oxidant. The use of oxygen as the oxidant is not disclosed nor is the co-presence of co-catalyst I salts as described herein disclosed. Selectivities to glycol of from about 4.5 to about 66% are disclosed. $H_2O_2$ oxidant in combination with $OsO_4$ is known as Milas reagent which can lead to non-selective oxidation of olefins as well as over oxidation. $H_2O_2$ is also substantially more expensive than oxygen or air. Accordingly, the uses of organohydroperoxides as well as $H_2O_2$ as oxidants are each associated with their own disadvantages.

U.S. Pat. No. 2,414,385 discloses the use of hydrogen peroxide and a catalytically active oxide, such as osmium tetroxide, dissolved in an essentially anhydrous, non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° C. and 21° C. Such low reaction temperatures drastically and disadvantageously, reduce the reaction rate to commercially unacceptable levels. At temperatures greater than 21° C., the formation of aldehydes, ketones, and acids is favored.

U.S. Pat. No. 2,773,101 discloses a method for recovering an osmium containing catalyst such as osmium tetroxide, by converting it to the non-volatile osmium dioxide form, distilling the hydroxylation product, re-oxidizing the osmium dioxide to the volatile osmium tetroxide, and then recovering the same by distillation. Suitable oxidizing agents used to oxidize olefins, and re-oxidize the osmium dioxide, include inorganic peroxides such as hydrogen peroxide, sodium peroxide, barium peroxide; organic peroxides, such as t-butyl peroxide or hydroperoxide, benzoyl peroxide; as well as other well known oxidizing agents such as oxygen, perchlorates, nitric acid, chlorine water and the like. As with other methods of the prior art, the above process yields undesirable by-products (see col. 1 line 55) thus reducing the selectivity of the process.

British Patent Specification No. 1,028,940 is directed to a process for regenerating osmium tetroxide from reduced osmium tetroxide by treatment of the latter with molecular oxygen in an aqueous alkaline solution. More specifically, it is disclosed that when osmium tetroxide is used by itself as an oxidizing agent, or as a catalyst in conjunction with other oxidizing agents, to oxidize hydrocarbons the osmium tetroxide becomes reduced, and in its reduced form is less active than osmium tetroxide itself. Consequently, by conducting the oxidation reaction in the presence of an alkaline medium and supplying oxygen to the medium throughout the process, the osmium tetroxide is maintained in a high state of activity. The oxidation products disclosed include not only ethylene glycol from ethylene but also organic acids from said compounds as vicinal glycols, olefins, ketones, and alcohols. While the pH of the alkaline medium is disclosed broadly for all possible reactions as varying from 7.5 to 12 for purposes of reoxidizing reduced osmium tetroxide, the pH employed in the example for preparing ethylene glycol is 9.5. If the pH is too high, a wide variety of products is produced as a result of over oxidation and/or degradation. Thus, the sensitivity of the process to the pH of the medium necessitates rigid pH which is economically disadvantageous.

U.S. Pat. No. 4,255,596 is directed to a process for preparing ethylene glycol in a homogeneous single-phase reaction medium using ethylbenzene hydroperoxide as the oxidizing agent dissolved in ethylbenzene and osmium tetroxide as the catalyst. The pH of the reaction medium is maintained at about 14 by the presence of tetraalkyl ammonium hydroxide. A small amount of water can dissolve beneficially in the medium to reduce by-product formation and improve selectivity to the glycol.

U.S. Pat. No. 4,049,724 describes the preparation of glycols from alkenes and from unsaturated alcohols in an aqueous system using osmium tetroxide and specifying stable and water-soluble aliphatic hydroperoxides, such as tert-butyl hydroperoxide, while a critical pH of 8 to 12 is maintained by a suitable combination of alkali metal buffering compounds. The preparation of propylene glycol utilizing tert-butyl hydroperoxide is exemplified in the patent at a selectivity based on the hydroperoxide of 45 percent.

None of the aforenoted patents disclose the osmium containing-co-catalyst system described herein.

See also: U.S. Pat. No. 3,317,592 (production of acids and glycols using oxygen as oxidant, $OsO_4$ as catalyst at pH 8-10); U.S. Pat. No. 3,488,394 (discloses hydroxylation of olefins by reacting olefin and hypochlorite in the presence of $OsO_4$); U.S. Pat. No. 3,486,478 (discloses reaction of hypochlorite and olefin in an aqueous medium and in the presence of $OsO_4$ catalyst to hydroxylate the olefin); U.S. Pat. No. 3,928,473 (hydroxylation of olefins to glycols with $O_2$ oxidant, octavalent osmium catalyst (e.g., $OsO_4$), and borates as promoter); U.S. Pat. No. 3,931,342 (discloses a process for recovering glycols from an aqueous solution containing alkali metal borate and osmium compounds (e.g., $OsO_4$); U.S. Pat. No. 3,953,305 (discloses use of $OsO_4$ catalyst for hydroxylating olefins which is regenerated by oxidizing hexavalent osmium with hexavalent chromium and electrochemically regenerating hexavalent chromium); U.S. Pat. No. 4,203,926 (discloses ethylbenzene hydroperoxide as oxidant used in two phase system to hydroxylate olefins in presence of $OsO_4$ and cesium, rubidium and potassium hydroxides); U.S. Pat. No. 4,217,291 (discloses the oxidation of Osmium (III) or (IV) in an ionic complex with oxygen and an alkali metal, ammonium, or tetra (-lower) alkyl ammonium cation to a valency of greater than +5+organo hydroperoxides); and U.S. Pat. No. 4,229,601 (discloses the use of cesium, rubidium and potassium hydroxides as promoters for $OsO_4$ catalyst and t-butyl hydroperoxide oxidant for hydroxylating olefins).

None of the aforenoted patents disclose the catalytically active metal oxide-co-catalyst I system described herein either alone or in combination with at least one co-catalyst II described herein.

SUMMARY OF THE INVENTION

In one aspect of the present invention, there is provided a process for hydroxylating at least one olefinic compound having at least one ethylenic unsaturation which comprises reacting said olefinic compound with oxygen and water in the presence of a catalyst composition in a manner and under conditions sufficient to convert at least one of said ethylenic unsaturation to its corresponding diol, said catalyst composition comprising:

(a) at least one catalytically active metal oxide wherein the metal of said oxide is selected from the group consisting of Os, Ti, Zr, Nb, Cr, Mo, W, Ru, Re, and Ir;

(b) at least one co-catalyst I transition metal salt having a cation and an anion wherein said cation is of a transition metal independently selected from the group consisting of Fe, Co, Ni, Cu, V, Cr, Mn, Sc, Ti, Mo, Ru, Rh, Pd, and W; and said anion is of a member independently selected from the group consisting of halide, carboxylate, aryloate, aryolate, psuedo halide, $R_5S^-$, $HS^-$, $R_5Se^-$, $HSe^-$, $HTe^-$, and $R_5Te^-$, $R_5$ being alkyl of from about 1 to about 10 carbons; and (c) optionally at least one co-catalyst II having a cation and an anion wherein said cation is of a member independently selected from the group consisting of alkali metal, alkaline earth metal, tetra hydrocarbyl ammonium, and tetra hydrocarbyl phosphonium, said hydrocarbyl group being selected from the group consisting of substituted and unsubstituted alkyl, aryl, alkaryl and aralkyl, and said anion is of a member independently selected from the group consisting of halide, carboxylate, aryloate, aryolate, pseuo halide, hydroxyl, $R_5S^-$, $HS^-$, $R_5Se^-$, $HSe^-$, $HTe^-$, and $R_5Te^-$ said $R_5$ being alkyl as defined above.

DESCRIPTION OF PREFERRED EMBODIMENTS

In accordance with the present invention, at least one olefin containing at least one ethylenic unsaturation is reacted with oxygen and water in the presence of a catalyst composition comprising a catalytically active metal oxide, at least one co-catalyst I as described herein, and optionally at least one co-catalyst II as described herein to convert at least one of said ethylenic unsaturation to its corresponding diol.

Olefins which can be hydroxylated in accordance with the present invention contain at least one ethylenic unsaturation and comprise any of the unsaturated aliphatic or alicyclic compounds well known in the art for undergoing such hydroxylation reactions. Typically, such compounds will contain from about 2 to about 20 carbons, preferably from about 2 to about 10 carbons, and most preferably from about 2 to about 5 carbons. Such compounds may be straight or branched chain, mono-olefinic, di-olefinic, or polyolefinic, conjugated or non-conjugated. They may be substituted with such groups as aryl, preferably aryl of from 6 to about 14 carbons, alkyl, preferably alkyl of from 1 to 10 carbons, or aralkyl and alkaryl wherein the alkyl and aryl portions thereof are as described above, as well as with functional groups such as hydroxyl, carboxyl and anhydride.

Typical of such olefins are those represented by the structural formula:

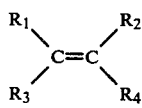   I wherein $R_1$, $R_2$, $R_3$, and $R_4$, which may be the same or different, are selected from the group consisting of hydrogen; substituted or unsubstituted: alkyl, aryl alkaryl, and aralkyl hydrocarbyl groups, said hydrocarbyl groups being preferably as defined immediately above; or any two or said $R_{1-4}$ groups together can constitute a cycloalkyl group typically of from about 4 to about 12, preferably from about 5 to about 8 carbons.

Representative olefins which can be hydroxylated and contain at least one ethylenic saturation include: ethylene, propylene, butene-1, butene-2, isobutene, pentene-1, pentene-2, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, oxtylcyclohexene, dodecyclohexene, acrolein, acrylic acid, 1,2,3,4-tetrahydrophthalic anhydride, methyl methacrylate, styrene, cholestrol, and the like.

The preferred olefins are ethylene, propylene, isobutylene, styrene, allyl alcohol and allyl chloride.

The most preferred olefins are propylene and ethylene.

The catalytically active metal oxide includes oxides, well known in the art as oxidation catalysts, such as transition metal oxides including those of Os, Ti, Zr, V, Nb, Cr, Mo, W, Ru, Re, and Ir.

Representative catalytically active metal oxides include: $OsO_2$, $OsO_4$, $TiO_2$, $ZrO_2$, $Nb_2O_3$, $V_2O_5$, $CrO_3$, $MoO_3$, $WO_3$, $Re_2O_7$, $IrO_2$, and the like.

The preferred catalytically active metal oxide is osmium tetroxide.

Co-catalyst I is a term used to refer to at least one organic or inorganic transition metal salt having an anion and a cation, wherein the anion of said salt includes halide, pseudo halide, carboxylate, aryloate, and aryolate and other anions described hereinafter.

More specifically, the cation transition metals of said co-catalyst I salts include those with a variable oxidation state such as Fe, Co, Ni, Cu, V, Cr, Mn, Sc, Ti, Mo, Ru, Rh, Pd, and W.

The preferred transition metal cations include those of Cu, Fe, Ni, Co, and Mn, most preferably Cu.

More specifically, the anion of co-catalyst I includes:

(a) halide ions such as fluoride, chloride, bromide, and iodide, preferably chloride, bromide, and iodide;

(b) carboxylate anions, typically carbonate anions represented by the structural formula:

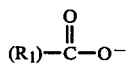   II wherein $R_1$ is selected from the group consisting of substituted and unsubstituted: alkyl, typically about $C_1$ to about $C_{10}$ alkyl, preferably about $C_1$ to about $C_5$ alkyl, and most preferably about $C_1$ to about $C_3$ alkyl, and aralkyl, typically aralkyl wherein the aryl group thereof is as defined in connection with Ar of structural formula III below and the alkyl group thereof if as defined immediately above; said $R_1$ substituents including hydroxyl; halide (i.e., F, Cl, Br, and I); ether groups, typically ether groups represented by the structural formulae $—O—R_2$, and $—R_3—O—R_2$ wherein $R_2$ and $R_3$ are independently selected from the group consisting of alkyl, typically about $C_1$ to about $C_{10}$ alkyl, preferably about $C_1$ to about $C_5$ alkyl and most preferably about $C_1$ to about $C_3$ alkyl; and ester groups, typically ester groups, represented by the structural formulae

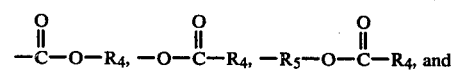

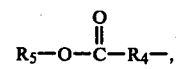

wherein $R_4$ and $R_5$ which may be the same or different are as defined in connection with $R_2$ and $R_3$;

(c) aryloate anions, typically aryloate anions represented by the structural formula:

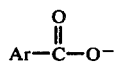   III wherein Ar is selected from the group consisting of substituted and unsubstituted: aryl, typically $C_6$ to about $C_{14}$ aryl, preferably $C_6$ to about $C_{10}$ aryl (e.g., $C_6$ aryl) and alkaryl, typically alkaryl wherein the alkyl group is as defined above in connection with $R_1$ being alkyl, and the aryl group thereof is as defined above, and wherein said substituents on the Ar group are as defined above in connection with $R_1$;

(d) aryolate anions, typically aryolate anions represented by the structural formula:

   IV wherein Ar is as described above in connection with structural formula III, and preferably is aryl; and (e) pseudo halide anions, defined herein to be selected from the group consisting of $SCN^-$, $CN^-$, $SeCN^-$, $TeCN^-$, $OCN^-$, and $CNO^-$; and (f) anions selected from the group consisting of $R_5S^-$, $HS^-$, $R_5Se^-$, $HSe^-$, $HTe^-$, and $R_5Te^-$, $R_5$ being alkyl typically about $C_1$ to about $C_{10}$ alkyl, preferably $C_1$ to $C_5$ alkyl.

In short, the co-catalyst I salt can be a single salt, or a mixture of salts and said salts can comprise any of the aforenoted transition metal cations associated with any of the aforenoted group (a)–(f) anions.

Representative examples of co-catalyst I salts include $FeF_3$, $FeCl_3$, $FeBr_3$, $FeF_2$, $FeCl_2$, $FeBr_2$, $FeI_2$, $CoCl_2$, $CoF_3$, $CoF_2$, $NiF_2$, $NiBr_2$, $NiI_2$, $NiCl_2$, $CuF_2$, $CuBr_2$, $CuI_2$, $CuF_2$, $CuI$, $CuCl$, $CuBr$, $VF_5$, $VF_4$, $VF_3$, $VF_2$, $VCl_4$, $VCl_3$, $VBr_4$, $VBr_3$, $VI_3$, $CrF_2$, $CrF_3$, $CrF_4$, $CrF_5$, $CrF_6$, $CrCl_3$, $CrCl_4$, $CrBr_3$, $CrBr_4$, $CrI_3$, $MnCl_2$, $MnCl_3$, $MnCl_4$, $MnBr_3$, $MnI_3$, $ScCl_3$, $ScBr_3$, $ScFl_3$, $TiCl_4$, $TiBr_4$, $TiF_4$, $MoCl_3$, $Mo_2Cl_{10}$, $MoBr_4$, $Mo_2F_9$, $MoF_6$, $MoF_5$, $RuF_5$, $RuF_3$, $RuF_4$, $RuF_6$, $RuCl_3$, $RuCl_4$, $RuCl_6$, $RuBr_6$, $RhF_3$, $RhF_4$, $RhF_6$, $PdF_2$, $PdCl_2$, $PdBr_2$, $PdI_2$, $WCl_6$, $WBr_5$, $WCl_3$, $WBr_3$, $WI_3$, copper acetate, copper naphthoate, copper benzoate, copper propanoate, iron acetate, iron benzoate, iron naphthoate, copper 4-ethyl benzoate, iron 4-butyl benzoate, nickel acetate, nickel benzoate, nickel naphthoate, copper decanoate, iron hexanoate, iron phthalocyanine, manganese phthalocyanine, copper phthalocyanine, nickel phthalocyanine, iron 2-(methoxymethyl)acetate, maganese 3-(ethoxy)-propanoate, copper 4-(propoxy carbonyl)butanoate, cobalt 3-(propyl carbonyl oxy)propanoate, vanadium 2-(methyl carbonyloxy methyl)acetate, copper 4-(ethoxy carbonyl methyl)butanoate, copper 4-(ethoxy methyl)benzoate, nickel 3-(propoxy)naphthoate, cobalt 4-(ethoxy carbonyl)benzoate, iron 2-(hydroxy)acetate, copper 2-chloro propanoate, vanadium 4-(bromo)benzoate, chromium 4-(hydroxy)benzoate, iron phenolate, copper naphtholate, nickel 4-chloro phenolate, vanadium 5-(hydroxy) naphtholate, $Fe(CN)_2$, $Cu(SeCN)_2$, $Ni(TeCN)_2$, $Cr(OCN)_3$, $Fe(CH_3S)_3$, $Cu(CH_3CH_2S)_2$, $Co(HS)_2$, $Ni(CH_3-CH_2-CH_2Se)_2$, $V(HSe)_3$, $Mn(HTe)_3$, $Ti(CH_3Te)_4$, and mixtures thereof.

The preferred co-catalyst I salts include copper:bromide, chloride iodide and acetate; iron:bromide, chloride, iodide, and acetate; maganese:iodide, chloride, bromide, and acetate and mixtures thereof.

Co-catalyst II is the term used herein to describe at least one organic or inorganic salt included within the classes of alkali and alkaline earth metal: halides, hydroxides, carboxylates, aryloates, aryolates, pseudo halides; tetra hydrocarbyl phosphonium: halides, hydroxides, carboxylates, aryloates, aryolates and pseudo halides; and tetra hydrocarbyl ammonium: halides, hydroxides, carboxylates, aryloates, aryolates, pseudo halides; and miscellaneous salts described hereinafter.

More specifically, the co-catalyst II salt preferably comprises at least one cation and an anion, said cation being independently selected from the group consisting of alkali metal cations including those of Li, Na, K, Rb, Cs, Fr; alkaline earth metal cations including those of Be, Mg, Ca, Sr, Ba, and Ra; and tetra hydrocarbyl phosphonium and ammonium cations represented by the respective structural formulae: $(R_6)_4P^+$ and $(R_6)_4N^+$ wherein each $R_6$ is a hydrocarbyl group independently selected from the group consisting of substituted and unsubstituted: alkyl, typically alkyl having from about 1 to about 30 carbons, preferably from about 1 to about 20 carbons, and most preferably from about 1 to about 10 (e.g., 1-5) carbons, aryl, preferably aryl having from 6 to about 14 carbons, and most preferably from 6 to about 10 carbons, and alkaryl and aralkyl wherein the aryl and alkyl groups thereof are as described immediately above; said $R_6$ substituents being as defined in connection with the substituents of $R_1$ described above. Accordingly, the term hydrocarbyl is intended to include both substituted and unsubstituted groups, and mixtures thereof.

The anion of co-catalyst II includes any of the anions described in conjunction with co-catalyst I, including halides, hydroxylate, carboxylate, aryloate, aryolate, pseudo halide, and "miscellaneous anions" defined herein to be selected from the group consisting of $R_5S^-$, $HS^-$, $R_5Se^-$, $H Se^-$, $HTe^-$, and $R_5Te^-$, $R_5$ being as described above.

More specifically, representative co-catalyst II alkali and alkaline earth metal halides include the Li, Na, K, Rb, and Cs, iodides, bromides, chlorides, and fluorides; and the Mg, Ca, Sr, and Ba, iodides, bromides, chlorides, and fluorides and mixtures thereof. Preferred co-catalysts II of this class include the Na, K, Rb, Cs, Mg, and Ca halides.

Suitable co-catalysts II alkali and alkaline earth metal hydroxides include LiOH, NaOH, KOH, RbOH, CsOH, $Ca(OH)_2$, $Ba(OH)_2$, $Mg(OH)_2$ and mixtures thereof.

Preferred co-catalysts II of this class include the Na, K, Rb, Mg, and Ca hydroxides.

Representative co-catalyst II alkali and alkaline earth metal: carboxylates, aryloates, and aryolates include sodium acetate, potassium acetate, calcium acetate, cesium acetate, magnesium acetate, potassium ethanoate, sodium propanoate, magnesium butanoate, strontium pentanoate, sodium benzoate, potassium benzoate, magnesium benzoate, calcium benzoate, sodium naphthoate, potassium naphthoate, beryllium naphthoate, sodium 4-(6-methyl-2-naphthyl)pentanoate, potassium 3-(7-methyl-1-naphthyl)-propanoate, magnesium 2-(4-propyl-1-benzyl)ethanoate, calcium phenolate, sodium naphtholate, potassium naphtholate, sodium 3-(ethoxy)-propanoate, potassium 4-(propoxy carbonyl)butanoate, calcium 3-(propyl carbonyl oxy)propanoate, magnesium 2-(methyl carbonyl oxy methyl)acetate, beryllium 4-(ethoxy carbonyl methyl)butanoate, cesium 4-(ethoxy methyl)benzoate, sodium 3-(propoxy)naphthoate, potassium 4-(ethoxy carbonyl)benzoate, barium 2-(hydroxy)acetate, rubidium 2-chloropropanoate, magnesium 4-bromobenzoate, magnesium phenolate, and mixtures thereof.

Preferred co-catalysts II of this class include the K, Rb, and Cs acetates.

Representative examples of co-catalyst II alkali and alkaline earth pseudo halides include NaSCN, KCN, NaSeCN, KSeCN, CsSeCN, NaTeCN, KTeCn, NaOCN, NaCNO, KOCN, KCNO, CsOCN, CsCNO, CsTeCN, $Mg(SeCN)_2$, $Mg(TeCN)_2$, $Mg(OCN)_2$, $Mg(CNO)_2$, $Ca(SeCN)_2$, $Ca(TeCN)_2$, $Ca(OCN)_2$, and $Ca(CNO)_2$, and preferably the Na, K, Rb, and Cs thiocyanates.

Representative examples of suitable co-catalyst II tetra hydrocarbyl ammonium and phosphonium halide, pseudo halide, hydroxide, carboxylate, aryloate, aryolate salts include tetra methyl ammonium bromide, tetra ethyl phosphonium chloride, tetra decyl phosphonium bromide, tetra phenyl ammonium chloride, tetra phenyl phosphonium bromide, dimethyl diethyl ammonium iodide, methyl triethyl phosphonium chloride, tetra butyl ammonium chloride, phenyl trimethyl ammonium bromide, phenyl trimethyl phosphonium chloride, phenyl triethyl ammonium iodide, phenyl triethyl phosphonium chloride, tetra ethyl ammonium hydroxide, tetra butyl ammonium hydroxide, tetra ethyl phosphonium hydroxide, phenyl triethyl ammonium hydroxide, phenyl trimethyl phosphonium hydroxide, tetraethyl ammonium acetate, tetra butyl phosphonium acetate, phenyl triethyl ammonium acetate, phenyl trimethyl phosphonium acetate, tetraethyl ammonium benzoate, phenyl trimethyl phosphonium benzoate, phenyl triethyl ammonium naphthoate, tetra ethyl ammonium phenolate, tetra butyl phosphonium naphtholate, tetra 2-(methoxy)ethyl phosphonium chloride, tetra 4-(propoxy methyl)phenyl ammonium bromide, di 3-(methoxy carbonyl)-propyl-diethyl phosphonium iodide, di 4-(ethyl carbonyloxy)butyl-dimethyl ammonium chloride, tetra 5-(ethoxy carbonyl methyl)pentyl phosphonium bromide, tetra 4-hydroxy butyl ammonium acetate, tetra 3-chloropropyl phosphonium acetate, tetra methyl ammonium thiocyanate, tetra ethyl phosphonium seleno cyanate, tetra (4-methyl phenyl)ammonium chloride, tetra (3-phenyl-1-propyl)phosphonium bromide.

Preferred co-catalysts II of this class include the unsubstituted tetra lower alkyl (e.g., $C_1$ to $C_5$ alkyl) ammonium or phosphonium hydroxides, iodides, bromides, fluorides, chlorides and acetates.

Representative co-catalyst II alkali, alkaline earth metal salts possessing the miscellaneous group of anions described above include $Na(CH_3S)$, $K(CH_3-CH_2-S)$, RbHS, CsHSe, $Ca(HTe)_2$, $Ba(CH_3Te)_2$, and mixtures thereof.

Representative co-catalyst II tetra hydrocarbyl ammonium and phosphonium salts possessing the miscellaneous groups of anions include $(CH_3-CH_2)_4PHSe$, $(CH_3)_4NHS$, $(C_6H_6)_4PHTe$, $(CH_3)_4PCH_3S$, $(CH_3-CH_2)_4N$ $CH_3-CH_2Se$, $(C_6H_6)_4PCH_3S$, $(CH_3-CH_2)_4NHSe$ and mixtures thereof.

The aforedescribed catalyst composition comprising at least the two components of catalytically active metal oxide, co-catalyst I and optionally the third component of co-catalyst II unexpectedly improves the selectivity of reactions of hydroxylating olefins with molecular oxygen up to about 100%. Although the exact mechanism and reason for this effect is not fully understood, it is considered that the results speak positively for themselves. However, the following is offered as an explanation of the mechanism for the observed catalytic effect in connection with the use of osmium tetroxide as the catalytically active metal oxide, although such explanation is not intended to be exhaustive of all possible mechanistic details. It is known that osmium tetroxide adds across the olefinic double bond of the compound to be hydroxylated to yield an intermediate cis-ester as follows:

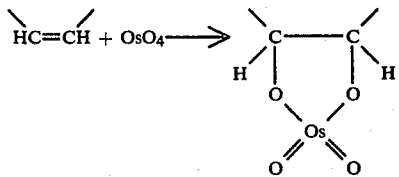

The osmium complex is now formally in the +6 oxidation state. The glycol product can be obtained from this complex by a reductive procedure which is commonly used in the well-known stoichiometric procedure wherein the osmium compound acts as the oxidant or it can be obtained by oxidative hydrolysis which is believed to be operating in the present invention.

Considering this system, it is believed that the anion of co-catalysts I and/or II acts to facilitate the hydrolysis of the glycolate while the transition metal of co-catalyst I mediates the oxidation of the osmium by molecular oxygen. The reoxidation is also believed to be facilitated by the pH and temperature of the reaction medium.

Similar mechanisms are believed to be operating in connection with the other catalytically active metal oxides described herein.

Thus, while the presence of co-catalyst I is essential to achieving substantial improvements in selectivity and/or yield of the hydroxylation reaction a still further improvement in these results can be obtained by the additional presence of co-catalyst II.

Accordingly, in view of the above explanation, it is recommended for best results that the most preferred valence of the transition metals of co-catalyst I as initially employed be that which represents the highest stable oxidation state thereof, since such metals must be capable of being reduced upon oxidizing the $Os^{+6}$. While this is not critical, it avoids the need in some instances to oxidize the transition metal in-situ so that it can be reduced.

It is also critical to have water present during the hydroxylation reaction since the water not only serves to hydrolyze the cis-ester intermediate but it is also believed to contribute one of the oxygen molecules constituting one of the hydroxyl groups in the resulting glycol. The source of this water, however, may vary. Thus, the water formed in-situ during the reaction can contribute to the water for the reaction. However, if more is needed it can be added separately.

In the practice of the present invention, the hydroxylation reaction is carried out in the presence of catalytic amounts of the catalytically active metal oxide, co-catalyst I and optional co-catalyst II. While any amount of each component in the two or three component catalyst system effective to catalyze the reaction is sufficient, it is preferred that such effective amounts constitute typically from about $10^{-5}$ to about $10^{-2}$ moles, preferably from about $5\times10^{-5}$ to about $5\times10^{-2}$ moles, and most preferably from about $10^{-4}$ to about $10^{-3}$ moles of the catalytically active metal oxide per mole of ethylenic unsaturation to be hydroxylated in the olefin; typically from about 1 to about 1,000 mole percent, preferably from about 100 to about 500 mole percent, and most preferably from about 200 to about 30 mole percent, co-catalyst I based on the total number of moles of metal in the catalytically active metal oxide employed; and typically from about 0 to about 500 mole percent, preferably from about 50 to about 300 mole percent, and most preferably from about 100 to about 150 mole percent, co-catalyst II, based on the total number of moles of the metal in the catalytically active metal oxide.

In the preferred embodiment wherein $OsO_4$ is employed as the catalytically active metal oxide, such catalytically effective amounts can range from about $10^{-5}$ to about $5\times10^{-1}$ moles, preferably from about $10^{-4}$ to about $10^{-3}$ moles $OsO_4$ per mole of ethylenic unsaturation to be hydroxylated in the olefin; typically from about 1 to about 1,000 mole percent, preferably from about 100 to about 500 mole percent, co-catalyst I, based on the total number of moles osmium in the $OsO_4$; and typically from about 0 to about 500 mole percent, preferably from about 100 to about 150 mole percent, co-catalyst II, based on the total number of moles of osmium in the $OsO_4$.

Also included in the term osmium tetroxide as used herein are osmium compounds which are converted to osmium tetroxide during the course of reaction such as salts thereof including K, Na, and Li osmates and the like.

While the hydroxylation reaction can be conducted in a heterogeneous system, the preferred mode for conducting the hydroxylation reaction is in a liquid reaction mixture, preferably provided as a homogeneous or substantially homogeneous medium by using an inert organic solvent to dissolve, where possible, whatever components are employed in the catalyst system and reactants. The solvent is entirely optional, however, and when present functions primarily to achieve even dispersal of heat in the reaction mixture. Partial immiscibility of the solvent with water is acceptable although not preferred. By an inert solvent is meant one which does not undergo oxidation during the course of the reaction.

Suitable inert organic solvents include aliphatic or aromatic alcohols having from 1 to about 10 carbon atoms, preferably tertiary alcohols, aliphatic or aromatic ketones having from 3 to about 10 carbon atoms, aliphatic or alicyclic ethers having from 2 to about 10 carbon atoms, glycols having from 2 to about 10 carbon atoms, N,N-dialkyl amides having from 3 to about 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and mixtures thereof.

The preferred solvents include those which are substantially or completely miscible with water such as t-butyl alcohol, methanol, and acetonitrile, as well as glycols and/or polyols derived from the olefin being hydroxylated.

The inert solvent is preferably employed in amounts sufficient to achieve a homogeneous solution with respect to at least the olefin and catalyst system. Typically such amounts can vary from about 0 to about 90% (e.g., 10 to 90%), preferably from about 20 to about 80%, and most preferably from about 20 to about 50%, by weight, based on the total weight of the reaction mixture.

Water is provided to, and/or is present in, the initial reaction mixture in at least a stoichiometric molar ratio with the molar amount of ethylenic unsaturation to be hydroxylated in the olefin. Such ratios preferably are also present in the reaction mixture at any given time after start-up. Accordingly, water is present in the reaction mixture at molar ratios, of water to ethylenic unsaturation to be hydroxylated in the olefin of from about 1:1 to about 100:1, preferably from about 1:1 to about 10:1, and most preferably from about 1:1 to about 2:1. Such molar ratios typically can be achieved by controlling the amount of water in the reaction mixture to be from about 2 to about 90%, preferably from about 15 to about 85%, and most preferably from about 20 to about 60%, by weight, based on the total weight of the reaction mixture. Preferably the amount of water employed is less than that which will cause separation of the reaction mixture into an aqueous phase and organic phase.

The pH of the reaction mixture during the hydroxylation reaction preferably should not be allowed to drop below about 4 otherwise the selectivity of the reaction drops drastically. Likewise, if the pH of the reaction exceeds about 10, over oxidation of the olefin may occur to an increasingly greater degree as the pH approaches 14. Accordingly, the pH of the reaction mixture typically is maintained between about 4 and 10, preferably between about 5 and about 9, and most preferably between about 6 and about 9 (e.g., 6 to 8). It is an advantage of the present invention that the pH of the reaction mixture using the ingredients described herein naturally falls within the range of about 6 to about 8 and consequently does not have to be controlled thereby simplifying the process. However, if the pH of the reaction mixture should drift for some reason within the undesirable ranges, conventional buffers or bases may be employed to limit such drift.

The primary oxidant employed in the present invention is molecular oxygen. Such oxygen can be added as a pure oxygen or as part of an oxygen containing gas such as air or some other oxygen containing gas having one or more inert components such as $CO_2$ or $N_2$ present therein. Generally, the oxygen containing gas is present within, preferably dissolved in, the reaction mixture in amounts sufficient to achieve hydroxylation of the olefin.

Accordingly, the molar ratio of oxygen to olefin ethylenic unsaturation can vary widely but for safety reasons it is preferably maintained outside explosive limits.

For example, when hydroxylating ethylene or propylene, if oxygen is in excess of stoichiometry, the ratio typically will be 98 weight % oxygen or more and 2% or less of the olefin. Preferably, however, the olefin is employed in excess, preferably large excess, of stoichiometry, and the oxygen concentration of the oxidizing gas typically will be about 10 weight % oxygen and about 90 weight % olefin. When oxygen is in excess of stoichiometry, olefin can be added during the reaction proceeds. On the other hand, where the olefin is in excess of stoichiometry, oxygen can be added during the reaction as the oxygen is consumed.

Accordingly, in view of the above, the oxygen containing gas preferably is dissolved in the reaction mixture in an amount sufficient to achieve a molar ratio of ethylenic unsaturation to be hydroxylated in the olefin to oxygen in excess of 1:1 typically up to as high as 100:1; and outside the explosive limits of the reaction mixture. It is to be noted, however, then when either olefin or $O_2$ is employed in substantial excess of stoichiometry for safety reasons the conversion in a batch process will necessarily be very low. This is not a problem in a continuous process since unreacted components are recycled.

The hydroxylation reaction is typically conducted at temperatures of from about 40° to about 150° C., preferably from about 60° to about 120° C., and most preferably from about 80° to about 100° C., to achieve high selectivities for the hydroxylated olefin.

At temperatures greater than the aforenoted ranges, the reaction rate increases substantially but this usually occurs at the expense of a significant reduction in selectivity. At very low reaction temperatures, e.g., below about 0° C., the reaction rate decreases to a commercially undesirable degree. Accordingly, while the reaction temperature is not critical and can vary over a wide range, one normally would not operate at temperature extremes outside the aforenoted ranges.

For the production of ethylene glycol, propylene glycol or any glycol derived from any unsaturated gaseous olefin, the latter may be bubbled through the reaction mixture containing the components described herein or it may be introduced under pressure. Likewise with the oxygen containing gas. However, it is preferred that the reaction takes place in the liquid phase. Consequently, sufficient pressure is preferably employed to maintain the gaseous reactants (i.e., olefin and oxygen) in the liquid phase.

Although the magnitude of the pressure is not critical, it determines the amount of the gaseous reactants that are present in the reaction mixture and therefore affects the rate of reaction. Accordingly, the total pressure of the gases in contact with the reaction mixture is typically controlled to be from about 200 to about 2,000 psig, preferably from about 300 to about 1500 psig, and most preferably from about 100 to about 1,000 psig at the aforenoted reaction temperatures. The partial pressure of each reactant gas, i.e., olefin and oxygen, can be controlled to achieve the aforenoted molar ratios. When the reactant olefin gas is ethylene, the partial pressure (at reaction temperatures) thereof is typically controlled to be from about 100 to about 2,000 psig, preferably from about 200 to about 1,500 psig, and most preferably from about 400 to about 1,000 psig; while when propylene is the reactant olefin, the partial pressure (at reaction temperatures) thereof is typically controlled to be from about 100 to about 2,000 psig, preferably from about 400 to about 1,500 psig and most preferably from about 400 to about 1,000 psig to provide a suitable reaction rate.

When the olefin reactant is a liquid or is dissolved in the reaction mixture under pressure, its concentration in the reaction mixture typically will vary from about 1 to about 90%, preferably from about 20 to about 80%, and most preferably from about 60 to about 80%, by weight, based on the total weight of the reactant mixture.

The hydroxylation reaction can be performed as a batch reaction, as a continuous reaction or as a semi-continuous reaction. In the batch reaction, the catalytically active metal oxide, e.g., $OsO_4$, is charged into the reaction vessel as a solution in the inert solvent along with the co-catalyst I and optional co-catalyst II, water, and olefin if in liquid form. The reaction vessel is then pressurized with oxygen and olefin if in gaseous form. It may be desirable to heat the liquid reaction mixture to reaction temperature prior to pressurizing with the reactant gases. The reaction is allowed to proceed to completion.

In the continuous process, the components can be introduced into the inlet of an elongated reactor at a rate such that substantially complete reaction will have taken place by the time the reaction mixture reaches the reactor outlet. The reaction can be carried out in a semi-continuous manner by metering the reactant mixture components into a series of two or more tank reactors at the appropriate rate to maintain the reactor liquid level.

The spent reaction mixture after removal of unreacted olefin is a solution of product glycol, by-products if any, solvent, water, and catalyst system components. The volatile components are distilled out of the reaction mixture into various fractions leaving non-volatile catalyst system components in the still. The product glycol is then separated from the high boiling distillate.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, selectivity, yield, and conversion are calculated as follows:

$$\% \text{ Selectivity} = \frac{\text{Moles of glycol}}{\text{Moles of Oxygenated Product}} \times 100$$

$$\% \text{ Conversion} = \frac{\text{Moles of product}}{\text{Moles of Olefin Charged}} \times 100$$

$$\% \text{ Yield} = \% \text{ conversion} \times \% \text{ selectivity}$$

Furthermore, all analysis of reaction products is conducted by gas chromatography.

EXAMPLE 1

Into a 300 ml titanium autoclave is charged 0.05 g of osmium tetroxide as a 0.5% solution thereof in t-butanol, 0.67 of $CuCl_2$ (co-catalyst I), 0.5 g tetraethyl ammonium bromide (co-catalyst II), 10.9 g of acetonitrile, and 76.6 g of water. Propylene (36.7 g) is added to the autoclave under a pressure of 140 psig, and the reaction mixture warmed to 100° C. Oxygen is added slowly (over a period of 20 min) until a pressure increase in the autoclave of 103 psig is obtained. The mixture is stirred for 140 minutes starting from the time of $O_2$ addition and then cooled to 25° C. The molar ratio of propylene to $O_2$ metered into the reaction mixure is about 20:1. The pH of the reaction mixture during the course of the reaction ranges from 5 to 7. The product solution is analyzed by gas chromatography and indicates the production 3.14 g of propylene glycol which is a yield of 5%, a selectivity of 99%, and a conversion of 5%, based on the propylene charged. No other detectible product such as ketones or polyols are generated under these conditions.

EXAMPLE 2

Into a 300 ml titanium autoclave is charged at room temperature (25° C.) 46.4 g propylene at a pressure of 160 psig, 0.05 g of osmium tetroxide. (0.5% t-butanol solution), 1.03 g sodium bromide (co-catalyst II) 66.2 g water, and 0.6 g of $CuCl_2$ (co-catalyst I). After warming the mixture to 100° C., to this solution is slowly added over a period of 10 minutes, oxygen until a pressure increase of 127 psig is obtained. The molar ratio of propylene to $O_2$ metered enter into the reaction mixture is about 20:1. (Note the slow addition of $O_2$ is to maintain its concentration outside explosive limits.) The reaction mixture is stirred at 100° C. for 2.5 hours upon completion of $O_2$ addition and then cooled to room temperature. The pH of the reaction mixture is 6.0. Propylene glycol (2.96 g) is produced in an amount which corresponds to a selectivity greater than 99%. The conversion of the reaction is 4%.

EXAMPLE 3

Into a 300 ml titanium autoclave is charged 0.2 mmole osmium tetroxide (0.5% t-butanol solution), 1.10 g $CuBr_2$ (co-catalyst I), 2.02 g of tetraethyl ammonium bromide (co-catalyst II), 79.9 g of $H_2O$, 6.7 g of acetonitrile and 36.5 g propylene at a pressure of 170 psig (25°

C.). The reaction mixture is then warmed to 100° C. To this solution is slowly added over a period of 15 minutes O₂ until a pressure increase of 127 psig is obtained. The molar ratio of propylene to O₂ meter into the reaction mixture is about 20:1, the solution is stirred at 100° C. for 2 hours upon completion of O₂ addition and then cooled to room temperature. The pH of the reaction mixture during the reaction is about 5. Propylene glycol (3.32 g) is produced and in an amount indicating in excess of 99% selectivity. The conversion is 4.4%.

EXAMPLE 4

The procedure of Example 1 is followed except that the materials added to the reaction autoclave are as follows: 0.05 g OsO₄ (0.5% t-butanol), CuCl₂ 0.4 g, NaCl 0.1 g, H₂O 43.4 g, methanol 19.9 g. The reaction mixture is warmed to 80° C. and 21.9 g of propylene (400 psig) is then added. Air is then introduced to the autoclave at 300 psig over a period of about 5 minutes. Olefin to O₂ ratio 60:1. The reaction mixture is then stirred for 2 hours upon completion of air addition. The pH of the reaction mixture during the reaction is about 5. The selectivity for propylene glycol is greater than 99% and the conversion is about 2%.

EXAMPLE 5

To a 300 ml titanium autoclave is charged 0.05 g (0.2 mmole) OsO₄, 0.66 g CuCl₂ 0.58 g NaCl, 11.7 g t-butanol, and 58.0 g ethylene at a pressure of 400 psig (25° C.) and the resulting mixture warmed to 100° C. Oxygen is added slowly over a period of 10 minutes until a pressure increase of 100 psig is obtained. The pH of the reaction mixture is about 5.5 The reaction mixture was stirred at 100° C. for 2.5 hours upon completion of O₂ addition and the products analyzed. Ethylene glycol (1.35 g, 21.8 mmole) is produced at 70% selectivity and 10% yield.

EXAMPLE 6

The following example illustrates the effect of omitting co-catalyst II from the reaction mixture.

Following the procedures of Example 5 to a 300 ml titanium autoclave is charged 0.05 g (0.2 mmole) OsO₄, 1.32 g CuCl₂, 18.8 g t-butanol, and 57.0 g H₂O. Ethylene is charged under a pressure of 400 psig (25° C.) and the reaction mixture is warmed. To 100° C. oxygen is added slowly over a period of about 5 minutes until a pressure increase of 100 psig is obtained. (Molar ratio of olefin: O₂ is about 20:1.) The reaction mixture (pH about 5) is stirred for 2.5 hours upon completion of O₂ addition at a temperature of 100° C. The product analysis (gas chromatography) indicates 0.72 g (11.0 mmole) ethylene glycol is produced at a selectivity of 39.2%, and 5% yield.

The following comparative examples are intended to illustrate the effect on glycol selectivity and yield when one omits co-catalyst I from the reaction components of the tri-component catalyst system.

COMPARATIVE EXAMPLE 1

The procedure of Example 2 is followed except that the materials added to the reaction autoclave are as follows: propylene 32.8 g at 160 psig (25° C.), OsO₄ 0.05 g (0.20 mmole) as 0.5% solution in t-butanol, tetraethylammonium bromide 1.06 g (5.0 mmoles), H₂O 75.8 g, acetonitrile 8.1 g. Oxygen is added until a pressure of 100 psig is obtained (olefin to O₂ molar ratio 20:1); with stirring at 100° C. for 2.5 hours upon completion of O₂ addition. The pH of the reaction mixture during reaction is about 5. In the absence of co-catalyst I, substantially no propylene glycol is formed, i.e., selectivity is about 0%, and conversion is about 0%.

COMPARATIVE EXAMPLE 2

The following comparative example illustrates the affect of omitting OsO₄ from the reaction mixture. The procedure of Example 2 is followed except that the materials added to the reaction autoclave are as follows: propylene 49.7 g (at 160 psig and 25° C.), CuBr₂ 1.10 g, tetraethylammonium bromide 1.05 g, H₂O 80 g, and acetonitrile 7.5 g. The reaction mixture is warmed to 100° C. Oxygen is then added until a pressure increase of about 100 psig is obtained (olefin to O₂ molar ratio 20:1). The resulting reaction mixture is stirred at 100° C. for 2.5 hours upon completion of O₂ addition. The pH of the reaction mixture during the reaction is about 5. Propylene glcol is formed in amount of about 0.30 g (4.0 mmoles). In the absence of the catalytically active metal oxide substantially no propylene glycol is formed.

As may be seen from a comparison of Example 5 with Example 6, the omission of co-catalyst II in Example 6 results in a reduction of selectivity.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for hydroxylating at least one olefinic compound having at least one ethylenic unsaturation which comprises reacting said olefinic compound with oxygen and water in the presence of a catalyst composition in a manner and under conditions sufficient to convert at least one of said ethylenic unsaturation to its corresponding diol, said catalyst composition comprising:
(a) at least one catalytically active metal oxide wherein the metal of said oxide is selected from the group consisting of Os, Ti, Zr, Nb, Mo, W, Ru, Re, and Ir;
(b) at least one co-catalyst I transition metal salt having a cation and an anion wherein said cation is of a transition metal independently selected from the group consisting of Fe, Co, Ni, Cu, V, Cr, Mn, Sc, Ti, Mo, Ru, Rh, Pd, and W; and said anion is of a member independently selected from the group consisting of halide, carboxylate, aryloate, aryolate, pseudo halide, $R_5S^-$, $HS^-$, $R_5Se^-$, $HSe^-$, $HTe^-$, and $R_5Te^-$, $R_5$ being alkyl of from about 1 to about 10 carbons; and
(c) optionally at least one co-catalyst II having a cation and an anion wherein said cation is of a member independently selected from the group consisting of alkali metal, alkaline earth metal, tetra hydrocarbyl ammonium, and tetra hydrocarbyl phosphonium, said hydrocarbyl group being selected from the group consisting of substituted and unsubstituted alkyl, aryl, alkaryl, and aralkyl and said anion is of a member independently selected from the group consisting of halide, carboxylate, aryloate, aryolate, pseudo halide, hydroxyl, $R_5S^-$, HS⁻, R₅Se⁻, HSe⁻, HTE⁻, and R₅Te⁻, said R₅ being alkyl as defined above.

2. The process of claim 1 wherein the olefinic compound contains from about 2 to about 20 carbons the metal of the catalytically active metal oxide is osmium; the cation of co-catalyst I is of a member independently selected from the group consisting of Cu, Fe, Ni, Co, and Mn; the anion of co-catalyst I is of a member independently selected from the group consisting of halide, carboxylate, aryloate, and aryolate; the cation of co-catalyst II when present is of a member selected from the group consisting of alkali metal, alkaline earth metal, tetra hydrocarbyl ammonium, and tetra hydrocarbyl phosphonium, said hydrocarbyl group being selected from the group consisting of alkyl, aryl, and mixtures thereof; and the anion of co-catalyst II when present, is of a member independently selected from the group consisting of halide, carboxylate aryloate and aryolate.

3. The process of claim 2 wherein said catalyst composition comprises at least one co-catalyst I and at least one co-catalyst II.

4. The process of claim 2 wherein the olefinic compound is selected from at least one member of the group consisting of ethylene and propylene; the catalytically active metal oxide is OsO₄; the co-catalyst I salt is selected from the group consisting of transition metal halide, transition metal acetate, transition metal benzoate and transition metal phenolate; and the co-catalyst II salt when present is selected from the group consisting of alkali metal halide, alkaline earth metal halide, alkali metal acetate, alkaline earth metal acetate, tetra hydrocarbyl ammonium halide wherein the hydrocarbyl group is selected from the group consisting of alkyl from about 1 to about 5 carbons, and aryl of from about 6 to about 10 carbons, tetra hydrocarbyl phosphonium halide, tetra hydrocarbyl ammonium acetate, and tetra hydrocarbyl phosphonium acetate wherein the respective hydrocarbyl groups are as defined above.

5. The process of claim 4 wherein the transition metal cation of co-catalyst I is of copper.

6. A process for hydroxylating olefins which comprises admixing to form a liquid reaction mixture:
(1) at least one olefinic compound having at least one ethylenic unsaturation;
(2) a catalyst composition comprising:
(a) at least one catalytically active metal oxide wherein the metal of said oxide is selected from the group consisting of Os, Ti, Zr, Nb, Mo, W, Ru, Re, and Ir;
(b) at least one co-catalyst I transition metal salt having a cation and an anion wherein said cation is of a transition metal independently selected from the group consisting of Fe, Co, Ni, Cu, V, Cr, Mn, Sc, Ti, Mo, Ru, Rh, Pd, and W; and said anion is of a member independently selected from the group consisting of halide, carboxylate, aryloate, aryolate, pseudo halide, R₅S⁻, HS⁻, R₅Se⁻, HSe⁻, HTE⁻, and R₅Te⁻, R₅ being alkyl of from about 1 to about 10 carbons; and
(c) optionally at least one co-catalyst II having a cation and an anion wherein said cation is of a member independently selected from the group consisting of alkali metal, alkaline earth metal, tetra hydrocarbyl ammonium, and tetra hydrocarbyl phosphonium, said hydrocarbyl group being selected from the group consisting of substituted and unsubstituted alkyl, aryl, alkaryl, and aralkyl and said anion is of a member independently selected from the group consisting of halide, carboxylate, aryloate, aryolate, pseudo halide, hydroxyl, R₅S⁻, HS⁻, R₅Se⁻, HSe⁻, HTE⁻, and R₅Te⁻, said R₅ being alkyl as defined above.

(3) an oxygen containing gas; and
(4) water in at least a stoichiometric molar ratio with the molar amount of ethylenic unsaturation to be hydroxylated in the olefinic compound; said admixing being conducted in a manner and under conditions sufficient to convert at least one of said ethylenic unsaturation to its corresponding diol.

7. The process of claim 6 wherein said liquid reaction mixture additionally comprises at least one inert organic solvent.

8. A process for directly hydroxylating an olefinic compound selected from the group consisting of ethylene, propylene and mixtures thereof which comprises contacting said olefinic compound with a substantially homogeneous reaction mixture having a pH of from about 4 to about 10, said reaction mixture comprising:
(a) at least one inert organic solvent in an amount of from about 0 to about 90% by weight based on the total weight of the reaction mixture;
(b) a catalyst composition comprising:
(i) osmium tetroxide in an amount of from about $10^{-5}$ to about $10^{-1}$ moles per mole of ethylenic unsaturation in the olefinic compound to be hydroxylated in said reaction mixture;
(ii) at least one co-catalyst I having a cation and an anion wherein said cation is of a transition metal selected from the group consisting of CU, Fe, Ni, Co, and Mn, and said anion is selected from the group consisting of halide, acetate, and benzoate, said co-catalyst I being dissolved in said reaction mixture in an amount of from about 1 to about 1,000 mole %, based on the total number of moles of osmium metal present in said reaction mixture and
(iii) at least one co-catalyst II selected from the group consisting of alkali metal halide, alkaline earth metal halide, alkali metal acetate, alkaline earth metal acetate, tetra alkyl ammonium halide, tetra alkyl ammonium acetate wherein the alkyl group contains from about 1 to about 5 carbons, tetra alkyl phosphonium halide and tetra alkyl phosphonium acetate wherein the alkyl group contains from about 1 to about 5 carbons, said co-catalyst II being dissolved in said reaction mixture in an amount of from about 0 to about 500 mole percent, based on the total number of moles of osmium metal present in said reaction mixture;
(c) an oxygen containing gas dissolved in said reaction mixture in an amount sufficient to achieve a molar ratio of ethylenic unsaturation in the olefinic compound to be hydroxylated in said reaction mixture to oxygen in excess of 1:1; and
(d) water in an amount sufficient to achieve a molar ratio of water to olefinic compound to be hydroxylated in said reaction mixture of from about 1:1 to about 100:1;

9. The process of claim 8 wherein co-catalyst II is selected from at least one member of the group consisting of sodium chloride, sodium bromide, potassium chloride, potassium bromide, tetra ethyl ammonium chloride, tetra ethyl phosphonium chloride, tetra ethyl ammonium bromide, tetra ethyl phosphonium bromide and mixtures thereof; co-catalyst I is selected from at least one member of the group consisting of $CuCl_2$, and $CuBr_2$; the inert solvent is selected from at least one member of the group consisting of ethylene glycol, propylene, glycol, acetonitrile, t-butanol, and methanol; and the pH of the reaction mixture is from about 5 to about 9.

* * * * *